(12) United States Patent
McDonald

(10) Patent No.: US 8,335,570 B2
(45) Date of Patent: Dec. 18, 2012

(54) ELECTRICAL STIMULATION LEADS HAVING RF COMPATIBILITY AND METHODS OF USE AND MANUFACTURE

(75) Inventor: Matthew Lee McDonald, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 232 days.

(21) Appl. No.: 12/568,914

(22) Filed: Sep. 29, 2009

(65) Prior Publication Data

US 2010/0094364 A1 Apr. 15, 2010

Related U.S. Application Data

(60) Provisional application No. 61/104,190, filed on Oct. 9, 2008.

(51) Int. Cl.
*A61N 1/16* (2006.01)

(52) U.S. Cl. .................................................. 607/116

(58) Field of Classification Search .......... 607/63, 607/115–117, 119, 121, 122; 600/372–374, 600/377, 378
See application file for complete search history.

(56) References Cited

U.S. PATENT DOCUMENTS

| | | | |
|---|---|---|---|
| 5,217,010 A | 6/1993 | Tsitlik et al. | |
| 5,366,496 A | 11/1994 | Dahl et al. | |
| 5,796,044 A | 8/1998 | Cobian et al. | |
| 5,957,970 A * | 9/1999 | Shoberg et al. | 607/122 |
| 6,181,969 B1 | 1/2001 | Gord | |
| 6,249,708 B1 * | 6/2001 | Nelson et al. | 607/122 |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 6,871,091 B2 | 3/2005 | Wilkinson et al. | |
| 6,901,292 B2 | 5/2005 | Hrdlicka et al. | |
| 6,944,489 B2 | 9/2005 | Zeijlemaker et al. | |
| 6,985,775 B2 | 1/2006 | Reinke et al. | |

(Continued)

FOREIGN PATENT DOCUMENTS

EP 1883449 A1 2/2008

(Continued)

OTHER PUBLICATIONS

U.S. Appl. No. 11/238,240, filed Sep. 29, 2005 (20 pgs.).

*Primary Examiner* — Carl H Layno
*Assistant Examiner* — Eugene Wu
(74) *Attorney, Agent, or Firm* — Frommer Lawrence & Haug LLP; Patrick R. Turner

(57) ABSTRACT

An implantable lead has an inner core, a plurality of coiled conductor guides, and a plurality of conductors. The inner core defines a plurality of lumens. Each coiled conductor guide defines a plurality of helical lumens. Each coiled conductor guide is disposed in a coiled arrangement over a portion of the inner core. Each of the conductors electrically couples at least one electrode to at least one terminal. At least one of the conductors includes a plurality of units. Each unit includes a first conductor segment extending along the inner core from a beginning point to a first position, a coiled conductor segment disposed at least partially in one of the lumens of the coiled conductor guides and extending from the first position to the second position, and a second conductor segment extending along the inner core from the second position to an endpoint.

20 Claims, 10 Drawing Sheets

U.S. PATENT DOCUMENTS

| | | |
|---|---|---|
| 7,123,013 B2 | 10/2006 | Gray |
| 7,164,950 B2 | 1/2007 | Kroll et al. |
| 7,174,219 B2 | 2/2007 | Wahlstrand et al. |
| 7,244,150 B1 | 7/2007 | Brase et al. |
| 7,257,449 B2 * | 8/2007 | Bodner .................. 607/122 |
| 7,363,090 B2 | 4/2008 | Halperin et al. |
| 7,445,605 B2 | 11/2008 | Overall et al. |
| 7,561,906 B2 | 7/2009 | Atalar et al. |
| 2003/0114905 A1 | 6/2003 | Kuzma |
| 2003/0204217 A1 | 10/2003 | Greatbatch |
| 2004/0059392 A1 | 3/2004 | Parramon et al. |
| 2004/0263173 A1 | 12/2004 | Gray |
| 2004/0263174 A1 | 12/2004 | Gray et al. |
| 2005/0070972 A1 | 3/2005 | Wahlstrand et al. |
| 2005/0079132 A1 | 4/2005 | Wang et al. |
| 2005/0165465 A1 | 7/2005 | Pianca et al. |
| 2005/0222642 A1 | 10/2005 | Przybyszewski et al. |
| 2005/0222647 A1 | 10/2005 | Wahlstrand et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2006/0025820 A1 | 2/2006 | Phillips et al. |
| 2006/0167496 A1 | 7/2006 | Nelson et al. |
| 2006/0200218 A1 * | 9/2006 | Wahlstrand .................. 607/116 |
| 2006/0247684 A1 | 11/2006 | Halperin et al. |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0293591 A1 | 12/2006 | Wahlstrand et al. |
| 2007/0010702 A1 | 1/2007 | Wang et al. |
| 2007/0088416 A1 | 4/2007 | Atalar et al. |
| 2007/0112398 A1 | 5/2007 | Stevenson et al. |
| 2007/0150007 A1 | 6/2007 | Anderson et al. |
| 2007/0150036 A1 | 6/2007 | Anderson |
| 2007/0161294 A1 | 7/2007 | Brase et al. |
| 2007/0179577 A1 | 8/2007 | Marshall et al. |
| 2007/0219595 A1 | 9/2007 | He |
| 2007/0239243 A1 | 10/2007 | Moffitt et al. |
| 2007/0288058 A1 | 12/2007 | Halperin et al. |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0065181 A1 | 3/2008 | Stevenson |
| 2008/0071313 A1 | 3/2008 | Stevenson et al. |
| 2008/0071320 A1 | 3/2008 | Brase |
| 2008/0119919 A1 | 5/2008 | Atalar et al. |
| 2008/0154348 A1 | 6/2008 | Atalar et al. |
| 2008/0161886 A1 | 7/2008 | Stevenson et al. |
| 2008/0167701 A1 | 7/2008 | John et al. |
| 2008/0200972 A1 | 8/2008 | Rittman et al. |
| 2008/0243218 A1 | 10/2008 | Bottomley et al. |
| 2008/0262584 A1 * | 10/2008 | Bottomley et al. ........... 607/119 |
| 2008/0281390 A1 | 11/2008 | Marshall |
| 2009/0118610 A1 | 5/2009 | Karmarkar et al. |
| 2009/0163980 A1 | 6/2009 | Stevenson |
| 2009/0171421 A1 | 7/2009 | Atalar et al. |
| 2009/0198314 A1 | 8/2009 | Foster et al. |
| 2009/0254152 A1 | 10/2009 | Atalar et al. |

FOREIGN PATENT DOCUMENTS

| | | |
|---|---|---|
| EP | 2025361 A1 | 2/2009 |
| EP | 2062525 A2 | 5/2009 |
| EP | 2062530 A2 | 5/2009 |
| EP | 2092952 A1 | 8/2009 |
| WO | 9221286 A1 | 12/1992 |
| WO | 9834678 A1 | 8/1998 |
| WO | 03090854 A1 | 11/2003 |
| WO | 2004066825 A2 | 8/2004 |
| WO | 2005030322 A1 | 4/2005 |
| WO | 2005032651 A1 | 4/2005 |
| WO | 2005062829 A2 | 7/2005 |
| WO | 2005/070494 A1 | 8/2005 |
| WO | 2005102444 A2 | 11/2005 |
| WO | 2005102445 A1 | 11/2005 |
| WO | 2005102446 A1 | 11/2005 |
| WO | 2005102447 A1 | 11/2005 |
| WO | 2005115531 A2 | 12/2005 |
| WO | 2006015040 A1 | 2/2006 |
| WO | 2006031317 A2 | 3/2006 |
| WO | 2006093685 A1 | 9/2006 |
| WO | 2006093686 A2 | 9/2006 |
| WO | 2006118640 A1 | 11/2006 |
| WO | 2006118641 A1 | 11/2006 |
| WO | 2006119492 A2 | 11/2006 |
| WO | 2006124481 A2 | 11/2006 |
| WO | 2007047966 A2 | 4/2007 |
| WO | 2007064739 A2 | 6/2007 |
| WO | 2007102893 A2 | 9/2007 |
| WO | 2007145671 A2 | 12/2007 |
| WO | 2008051913 A1 | 5/2008 |
| WO | 2008077037 A2 | 6/2008 |
| WO | 2008115383 A2 | 9/2008 |
| WO | 2008115426 A1 | 9/2008 |
| WO | 2008134634 A1 | 11/2008 |
| WO | 2008140624 A2 | 11/2008 |
| WO | 2009100003 A1 | 8/2009 |
| WO | 2009117069 A2 | 9/2009 |

* cited by examiner

ELECTRICAL STIMULATION LEADS HAVING RF COMPATIBILITY AND METHODS OF USE AND MANUFACTURE

CROSS-REFERENCE TO RELATED APPLICATIONS

This application is a utility patent application based on a previously filed U.S. Provisional Patent Application, Ser. No. 61/104,190 filed on Oct. 9, 2008, the benefit of which is hereby claimed under 35 U.S.C. §119(e) and incorporated herein by reference.

FIELD

The present invention is directed to the area of implantable electrical stimulation systems and methods of making and using the systems. The present invention is also directed to implantable electrical stimulation leads having RF compatibility and implantable electrical stimulation systems that include the lead, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

In one embodiment, an implantable lead includes an inner core, a plurality of electrodes disposed at a distal end of the implantable lead, and a plurality of terminals disposed at a proximal end of the implantable lead. The inner core has a proximal end, a distal end, and a longitudinal length. The inner core also defines a plurality of lumens. The implantable lead also includes a plurality of coiled conductor guides and a plurality of conductors. Each coiled conductor guide has a first end and a second end and defines a plurality of helical lumens. Each coiled conductor guide is disposed in a coiled arrangement over a portion of the inner core. Each of the conductors electrically couples at least one of the electrodes to at least one of the terminals. At least one of the conductors includes a plurality of units. Each unit includes a first conductor segment extending along the inner core from a beginning point to a first position, a coiled conductor segment disposed at least partially in one of the lumens of the coiled conductor guides and extending from the first position to the second position, and a second conductor segment extending along the inner core from the second position to an endpoint.

In another embodiment, an electrical stimulating system includes a lead, a control module, and a connector. The lead has a distal end and a proximal end. The lead includes an inner core with a proximal end, a distal end, and a longitudinal length. The inner core defines a plurality of lumens. The lead also includes a plurality of electrodes disposed on the distal end of the lead and a plurality of terminals disposed on the proximal end of the lead. The lead further includes a plurality of coiled conductor guides and a plurality of conductors. Each coiled conductor guide has a first end and a second end and defines a plurality of helical lumens. Each coiled conductor guide is disposed in a coiled arrangement over a portion of the inner core. Each conductor electrically couples at least one of the electrodes to at least one of the terminals. At least one of the conductors includes a plurality of units. Each unit includes a first conductor segment extending along the inner core from a beginning point to a first position, a coiled conductor segment disposed at least partially in one of the lumens of the coiled conductor guides and extending from the first position to the second position, and a second conductor segment extending along the inner core from the second position to an endpoint. The control module is configured and arranged to electrically couple to the proximal end of the lead. The control module includes a housing and an electronic subassembly disposed in the housing. The connector is configured and arranged for receiving the lead. The connector has a proximal end, a distal end, and a longitudinal length. The connector includes a connector housing and a plurality of connector contacts disposed in the connector housing. The connector housing defines a port at the distal end of the connector. The port is configured and arranged for receiving the proximal end of the lead. The connector contacts are configured and arranged to couple to at least one of the plurality of terminals disposed on the proximal end of the lead.

In yet another embodiment, a method for making an implantable lead includes disposing a plurality of electrodes on a distal end of a lead, disposing a plurality of terminals on a proximal end of the lead, and coupling the electrodes to the terminals using a plurality of conductors. The lead includes an inner core defining a plurality of lumens and at least one coiled conductor guide defining a plurality of helical lumens. The at least one coiled conductor guide is disposed in a coiled arrangement over a portion of the inner core. At least one of the conductors includes a plurality of units. Each unit includes a first conductor segment extending along the inner core from a beginning point to a first position, a coiled conductor segment disposed at least partially in one of the lumens of the coiled conductor guides and extending from the first position to the second position, and a second conductor segment extending along the inner core from the second position to an endpoint.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads having RF compatibility and implantable electrical stimulation systems that include the lead, as well as methods of making and using the leads and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393,991; and 11/396,309, all of which are incorporated by reference.

Figure 1:
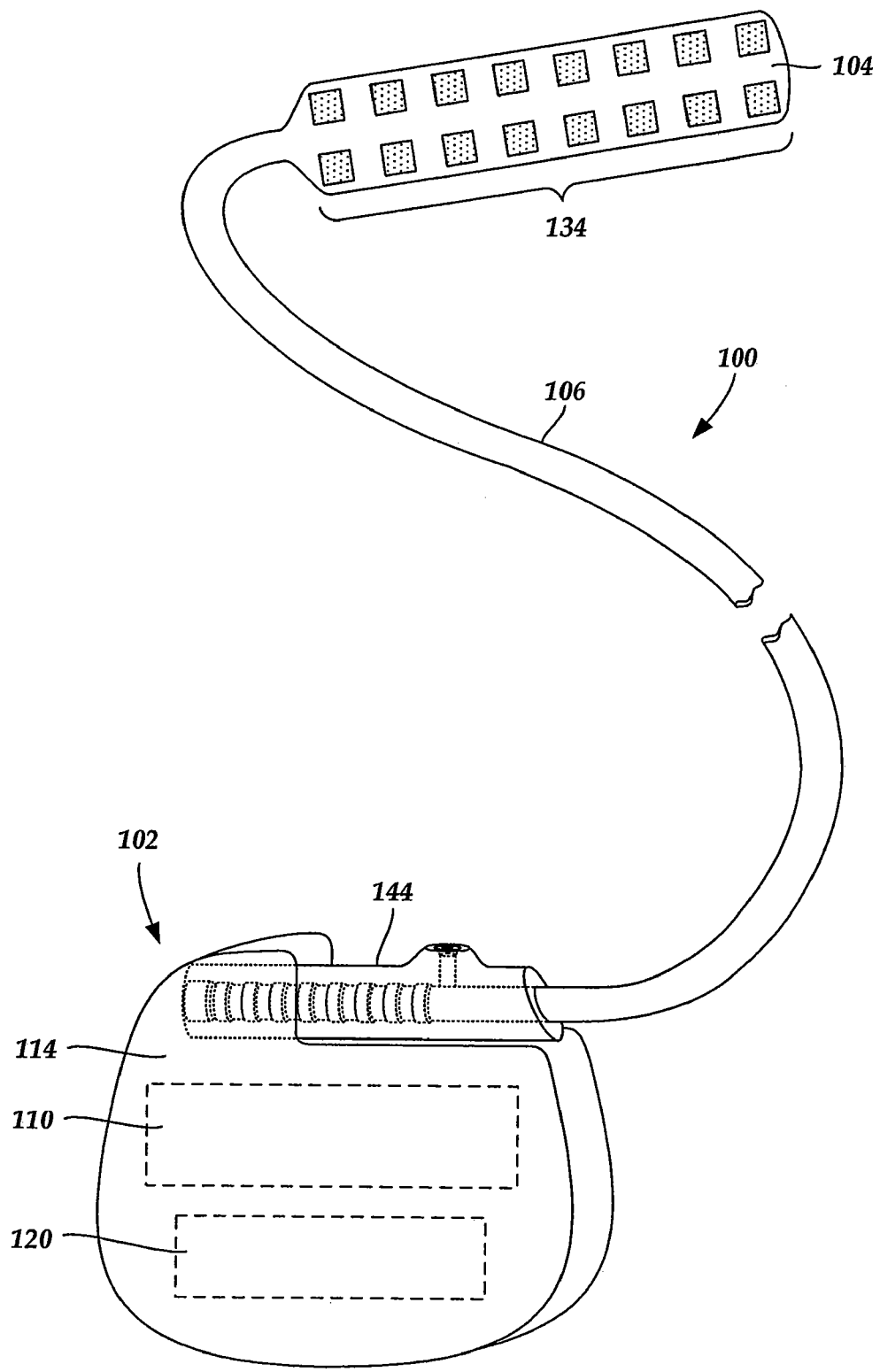
FIG. 1 is a schematic view of one embodiment of an electrical stimulation system, according to the invention.
Figure 2:
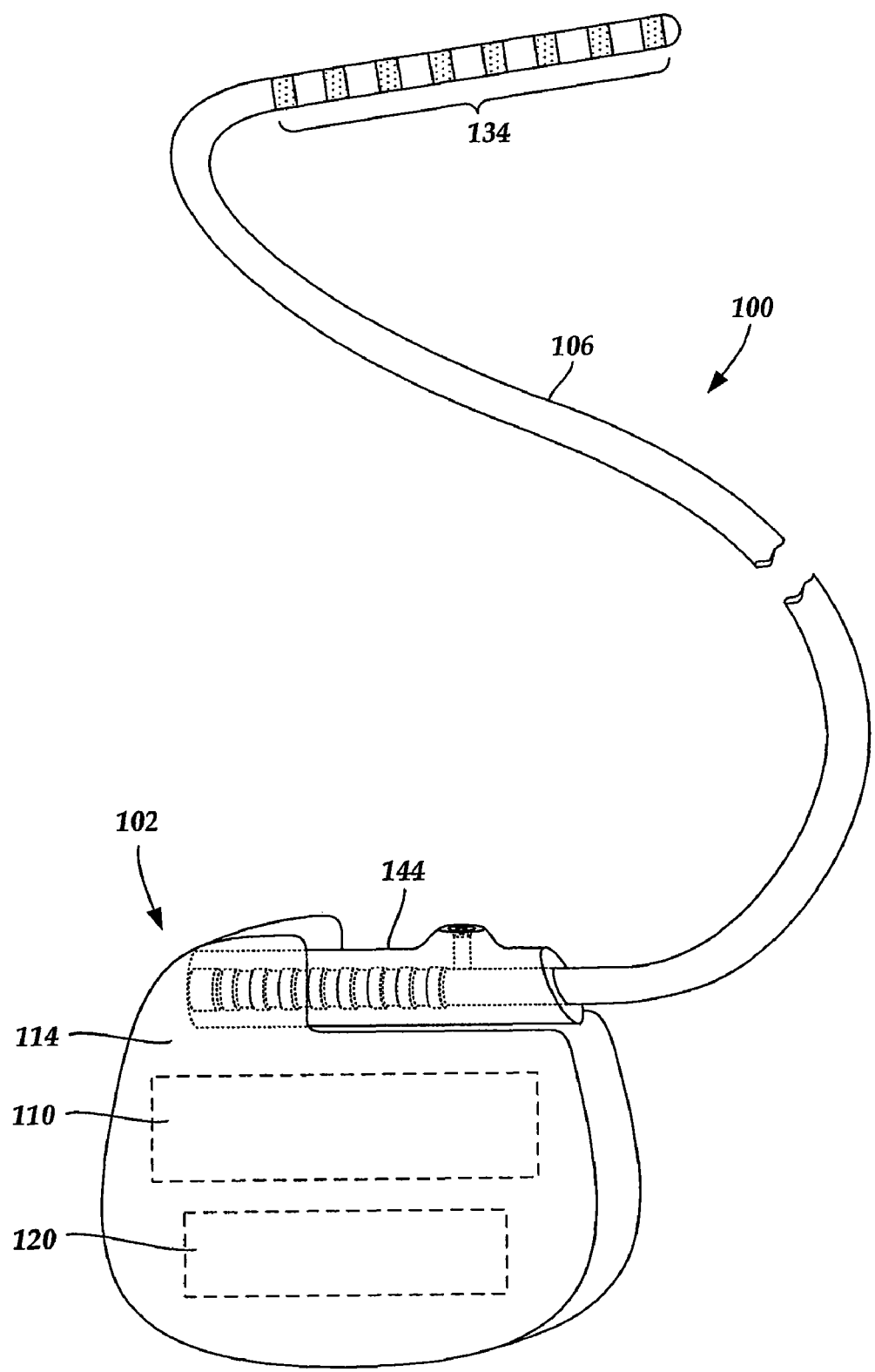
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via conductive contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding conductive contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as conductive contacts on a lead extension, an operating room cable, or an adaptor). Conductive wires ("conductors") (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within an body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
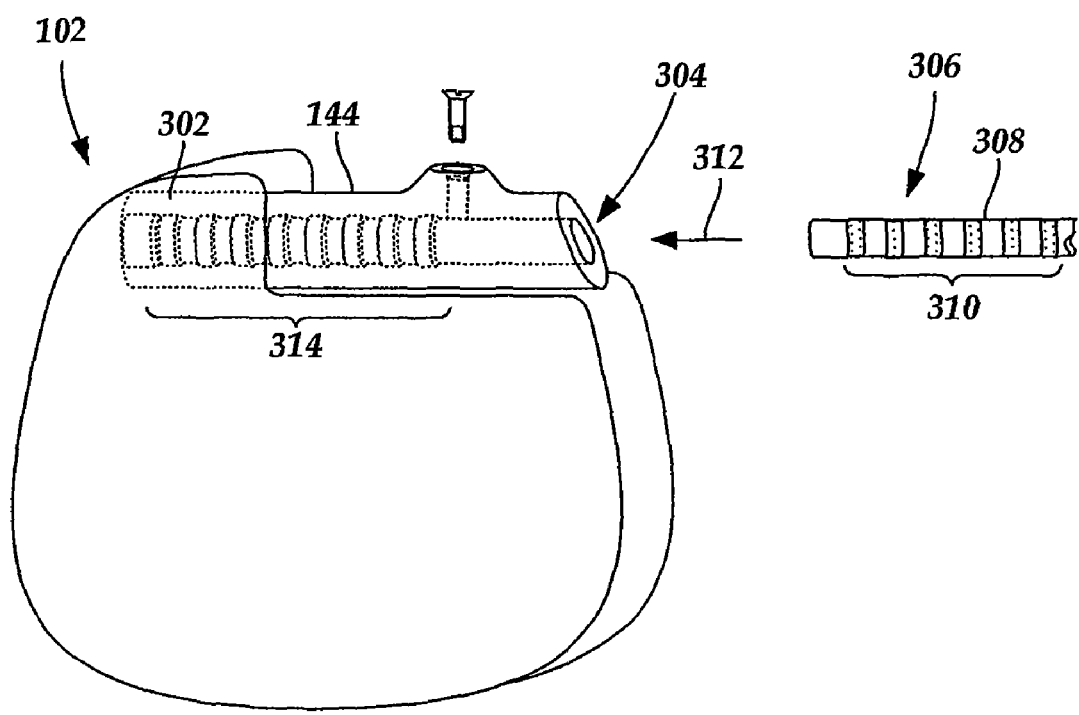
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of conductive contacts 314 for each port 304. When the lead 308 is inserted into the port 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532, 844, which are incorporated by reference.

Figure 3B:
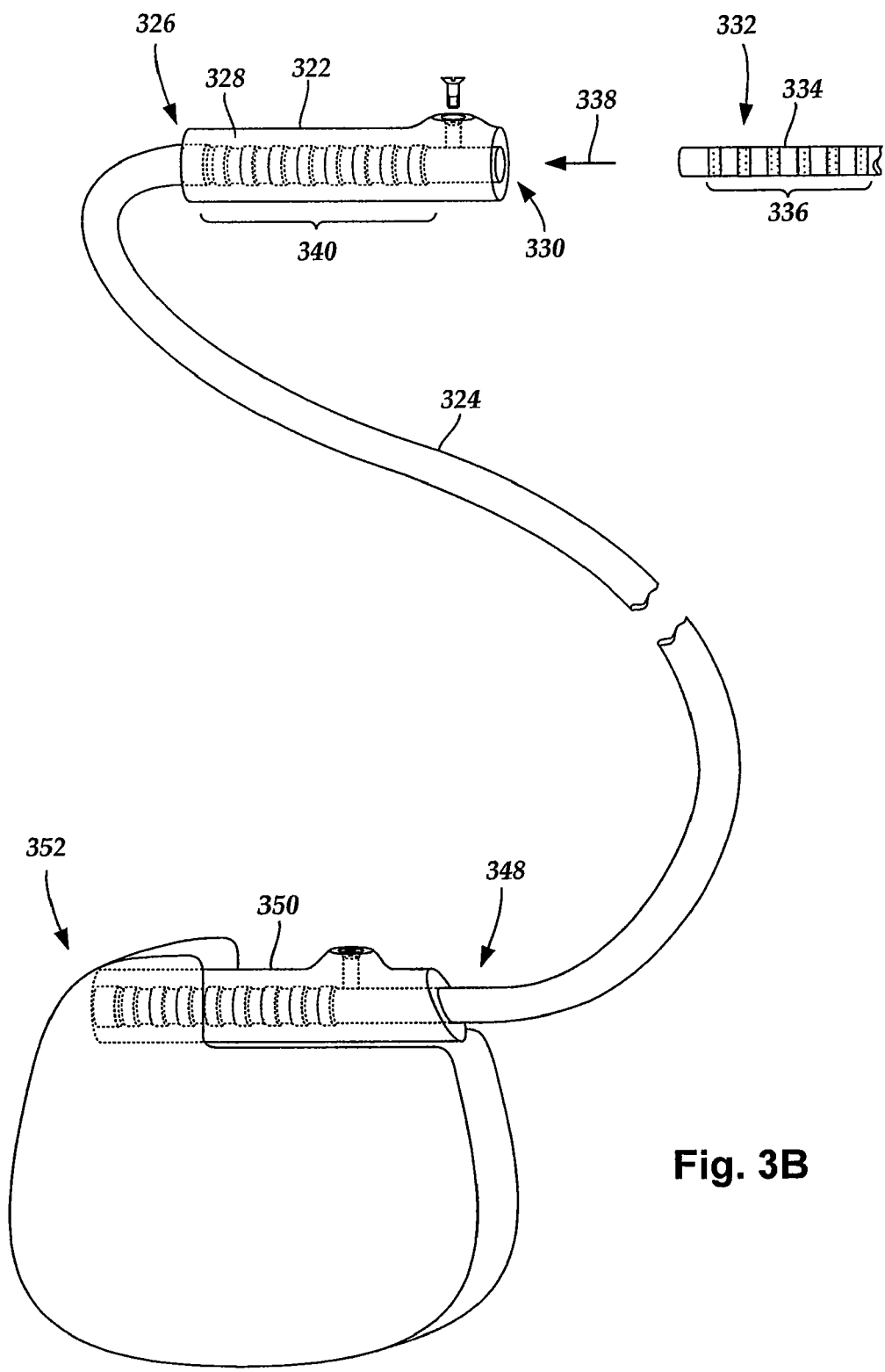
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of conductive contacts 340. When the lead 334 is inserted into the port 330, the conductive contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) that electrically couple the conductive contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

One or more of the conductors connecting at least one electrode to a terminal (or other conductive contact) can be arranged in a conductor path to eliminate or reduce the effect of RF irradiation, such as that generated during magnetic resonance imaging ("MRI"). The conductor includes a plurality of units. In at least some embodiments, the units are disposed in series along the conductor. In some embodiments, the units are disposed along a single continuous conductor. In other embodiments, the units are separate conductive elements electrically coupled together.

Each unit includes at least three conductor segments. First, each unit includes a first substantially-straight conductor segment ("first conductor segment") that extends in a first direction along a longitudinal length of the lead (or lead extension) from a beginning point to a first position. Second, each unit includes a coiled conductor segment that extends from the first position back towards (and possibly past) the beginning point to a second position. Third, each unit includes a second substantially-straight conductor segment ("second conductor segment") that extends in the first direction from the second position to an endpoint. The units may be electrically continuous such that the endpoint of a first unit is the beginning point of the next consecutive unit. At least one of the beginning points may be a terminal or an electrode (or other conductive contact). Likewise, at least one of the endpoints may be a terminal or an electrode (or other conductive contact).

In at least some embodiments, the length of conductor used in the coiled conductor segment (i.e., the length of the coiled conductor segment if it were straightened out) is at least 1.5, 1.75, 1.9, 2, 2.1, 2.25, or 2.5 times the length of either the first conductor segment or the second conductor segment. It will be recognized, however, that this ratio of lengths may vary among embodiments, particularly if the thickness of the conductor or thickness of insulation on the conductor is different for the different segments.

In at least some embodiments, the conductor segments are all formed from the same length of insulated wire. The wire may have a single filament or be multi-filar. In at least some embodiments, two or more of the conductor segments can be individual pieces of wire that are electrically coupled (e.g., soldered or welded) together.

Figure 4:
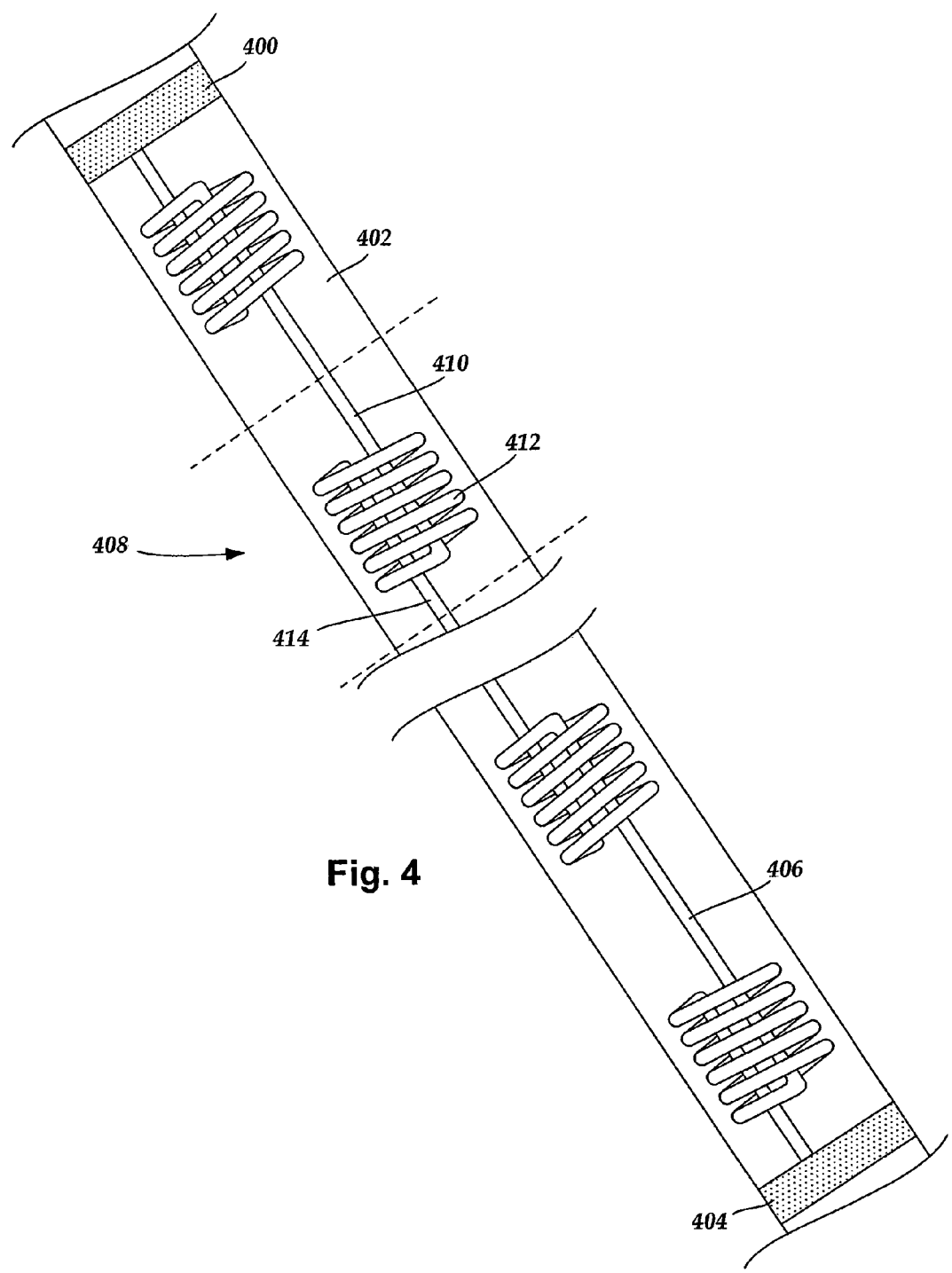
FIG. 4 is a schematic view of one embodiment of a terminal and electrode of a lead (or terminal and conductor contact of a lead extension) coupled together by a conductor with a conductor path that includes a plurality of units, each unit including a first substantially-straight conductor segment, a coiled conductor segment, and a second substantially-straight conductor segment, according to the invention.

FIG. 4 schematically illustrates one embodiment of a conductor 406 electrically coupling a terminal 400 disposed at or near a proximal end of a lead (or lead extension) 402 to an electrode (or conductive contact) 404 disposed at or near a distal end of the lead (or lead extension) 402. The conductor 406 includes a plurality of units, such as unit 408 (shown in FIG. 4 between two dashed lines), in series. Each unit includes a first conductor segment 410, a coiled conductor segment 412, and a second conductor segment 414. Many different numbers of units may be disposed on the conductor 406 between the terminal 402 and the electrode or conductive contact 404 including, for example, two, three, four, five, six, seven, eight, nine, ten, twelve, fifteen, twenty, twenty-five, thirty, forty, fifty, or more units. It will be understood that many other numbers of units may be employed as well.

It will be understood that a lead typically includes multiple terminals, multiple electrodes, and multiple conductors and a lead extension typically includes multiple terminals, multiple conductive contacts, and multiple conductors. Each of the conductors can include one or more units, or only a subset may include one or more units, the remaining conductors having a different arrangement (for example, a single conductor segment between the terminal(s) and electrode(s)/conductive contact(s)). It will be further understood that the term "substantially-straight conductor segment" means that the conductor segment is not coiled. A "substantially-straight conductor segment" may be curved, particular when the lead itself is curved (see, for example, FIG. 1). It will also be understood that the same conductor arrangements can be used to couple a terminal on a proximal end of a lead extension to a terminal on the distal end of a lead extension.

A variety of methods can be used to arrange the conductor segments 410, 412, and 414 of the conductors within the lead (or lead extension) 402. For example, a portion of one or both of the first and second coiled conductor 410 or 414 segments can be disposed between the coils of the coiled segment 412. Alternatively or additionally, one or both of the first and second conductor segments 410 or 414 can be disposed outside of the coils of the coiled conductor segment 412.

In at least some embodiments, one or more conductors of a lead (or lead extension) may be configured and arranged to employ a plurality of units such as, for example, the conductor configuration shown in FIG. 4. In at least some embodiments, the lead (or lead extension) may include an inner core with one or more interior lumens (preferably, multiple interior lumens). One or both of the first and second conductor segments of the conductor(s) may extend along at least a portion of one or more of these interior lumens, with the coiled conductor segment disposed in one or more exterior lumens of one or more coiled conductor guides wrapped around the inner core. The interior lumens may each include one or more openings that allow the conductor(s) to pass between an inner core and an exterior lumen.

Figure 5A:
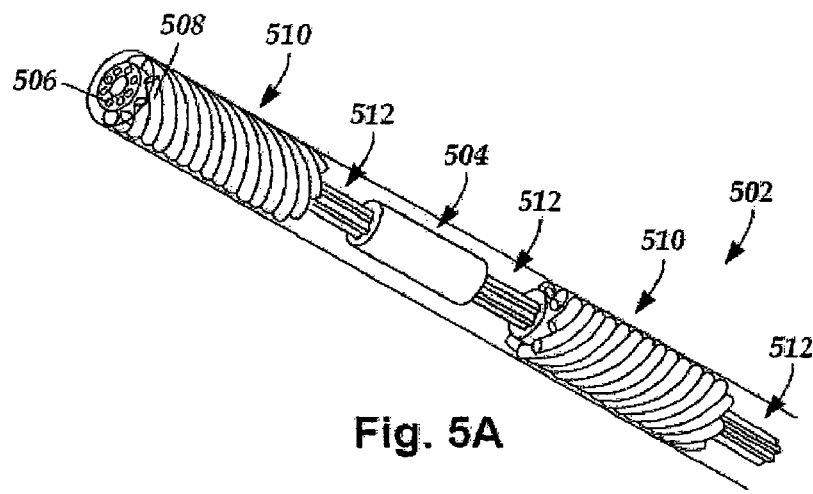
FIG. 5A is a schematic perspective view of one embodiment of a portion of a lead (or a lead extension), the lead (or the lead extension) including an inner core configured and arranged for housing first substantially-straight conductor segments or second substantially-straight conductor segments of units, and exterior lumens disposed in coiled conductor guides wrapped around the inner core, according to the invention.

FIG. 5A is a schematic perspective view of one embodiment of a portion of a lead 502. The lead 502 includes an inner core 504 which defines interior lumens, such as interior lumen 506. The lead 502 also includes exterior lumens, such as exterior lumen 508, defined in coiled conductor guides 510 wrapped around portions of the inner core 504. In at least some embodiments, the interior lumens include one or more open sections 512. In at least some embodiments, the open sections 512 are positioned on either end of the coiled conductor guides 510. In at least some embodiments, the open sections 512 facilitate arrangement of conductor paths for conductors disposed in the interior and exterior lumens. For example, in some embodiments, an end of a conductor disposed in an interior lumen may be routed through an exterior lumen and back into either the same interior lumen, or a different conductor lumen, or through another portion of the lead 502.

In at least some embodiments, the coiled conductor guides 510 are configured and arranged so that the exterior lumens are wrapped around the inner core 504 in a single layer. In at least some embodiments, the exterior lumens are wrapped in a helical orientation. In at least some embodiments, the ends of the coiled conductor guides 510 may be coupled to the inner core 504 to insulate conductors disposed in the interior and exterior lumens. The ends of the coiled conductor guides 510 may be coupled to the inner core 504 using many different techniques including, for example, overmolding, potting, adhesive, and the like.

In at least some embodiments, the interior lumens, such as interior lumen 506, are configured and arranged for housing the first conductor segments or the second conductor segments of units and the exterior lumens are configured and arranged for housing the coiled conductor segments of units. In at least some embodiments, when a conductor extends along a conductor path through one or more interior lumens and an exterior lumen, as described below (with reference to FIG. 5B), the conductor forms units (see FIG. 4). It will be understood that, although described in FIGS. 5A-9C as being implemented in the lead 502, units can similarly be implemented in lead extensions.

Figure 5B:
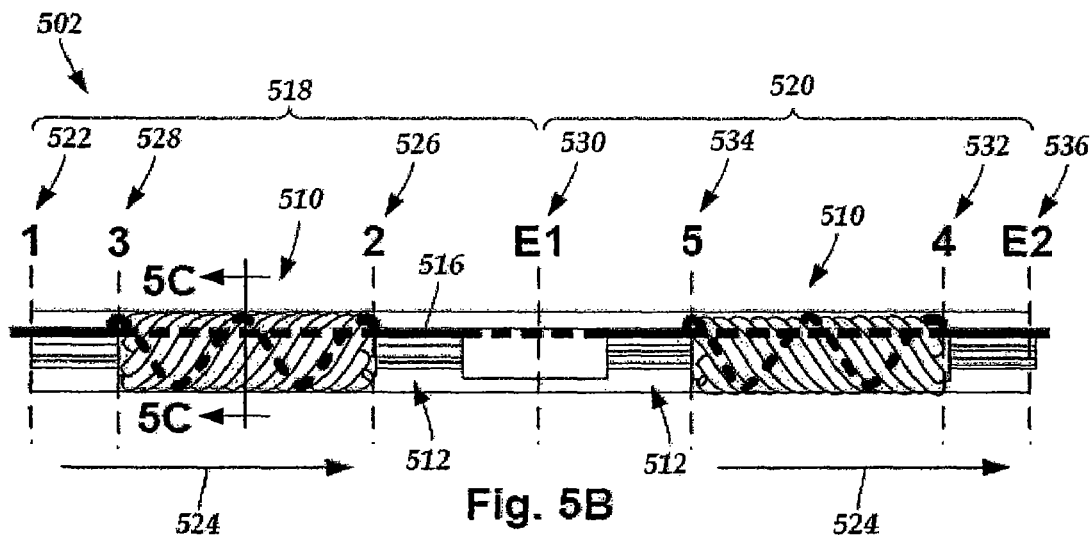
FIG. 5B is a schematic side view of one embodiment of a portion of the lead (or the lead extension) shown in FIG. 5A, the lead including an exemplary conductor path through two units, according to the invention.

FIG. 5B is a schematic side view of one embodiment of the portion of the lead 502. In FIG. 5B, an exemplary conductor 516 is shown extending along a conductor path through two adjacent units 518 and 520 that approximate an adjacent two-unit portion of the electrical coupling shown in FIG. 4.

The conductor 516 begins unit 518 at beginning point "1" 522 and extends in a first direction, indicated in FIG. 5B by directional arrow 524. The conductor 516 extends to a first position "2" 526. In at least some embodiments, (as shown in FIG. 5B) the conductor 516 extends from beginning point "1" 522 to first position "2" 526 in one of the interior lumens. In alternate embodiments, the conductor 516 extends from beginning point "1" 522 to first position "2" 526 within the non-conductive material of the lead 502. In yet other alternate embodiments, the conductor 516 extends from beginning point "1" 522 to first position "2" 526 along a path external the coiled conductor guides 510.

The conductor 516 then extends within an exterior lumen (e.g., 508 in FIG. 5A) from the first position "2" 526 to a second position "3" 528. In at least some embodiments, the conductor 516 extends helically within the exterior lumen in a direction that is approximately opposite of the first direction 524. The conductor 516 then extends in a first direction 524 to an endpoint "E1" 530, the endpoint of the unit 518. In at least some embodiments, the conductor 516 extends from the second position "3" 528 to the endpoint "E1" 530 in one of the interior lumens (or alternately in non-conductive material of the lead 502 or along a path external to the exterior lumens). The endpoint "E1" 530 can also be the beginning point for the unit 520. Note that the endpoint "E1" 530 is of arbitrary positioning and may be thought of as existing anywhere on the conductor path between the second position "3" 528 of the first unit 518 and first position "4" 532 of the second unit 520. Note also, that when the conductor 516 extends within an interior lumen from second position "3" 528 to a first position "4" 532, the conductor 516 may extend through one or more open sections 512.

In at least some embodiments, the conductor 516 extends along unit 520 in a similar manner as the unit 518. For example, the conductor 516 may extend through the unit 520 by extending in the first direction 524, in one of the interior lumens (or alternately in non-conductive material of the lead 502 or along a path external to the exterior lumens), from the endpoint/beginning point "E1" 530 to first position "4" 532. The conductor 516 then may extend within an exterior lumen (e.g., 508 in FIG. 5A) from the first position "4" 532 to a second position "5" 534, and then in the first direction 524 from the second position "5" 534 to endpoint "E2" 536 in one of the interior lumens (or alternately in non-conductive material of the lead 502 or along a path external to the exterior lumens).

Figure 5C:
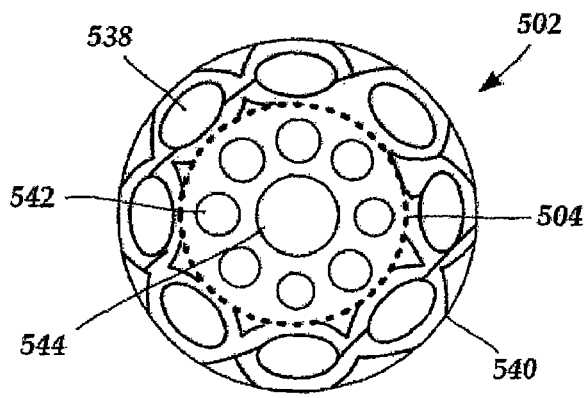
FIG. 5C is a schematic transverse cross-sectional view of one embodiment of a portion of the lead (or lead extension) shown in FIG. 5B, according to the invention.

FIG. 5C is a schematic transverse cross-sectional view of one embodiment of a portion of the lead 502. The lead 502 includes the inner core 504, outlined in FIG. 5C by a dotted circle, and exterior lumens, such as exterior lumen 538 defined in a coiled conductor guide 540 wrapped around the inner core 504. The inner core 504 defines interior lumens, such as interior lumen 542. In at least some embodiments, the inner core 504 may also define one or more central lumens, such as central lumen 544. In at least some embodiments, the diameters of the interior lumens are approximately equal to the diameters of the exterior lumens (e.g., the diameters of the interior lumens are no more than 1.2 times the diameter of the exterior lumens and at least 0.8 times the diameter of the exterior lumens).

In at least some embodiments, for each unit of a conductor path two conductor segments extend along the inner core 504 (or external to the exterior lumens), whereas a single conductor segment extends along the exterior lumens. For example, when eight conductors are disposed in the lead 502, sixteen conductor segments may extend along the inner core 504 (or external to the exterior lumens) and eight conductor segments may extend along the exterior lumens.

Figure 6A:
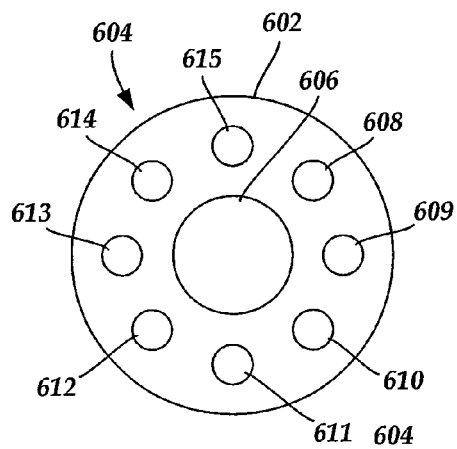
FIG. 6A is a schematic transverse cross-sectional view of one embodiment of an inner core of a lead (or lead extension), the inner core including a plurality of interior lumens, each interior lumen configured and arranged for housing a single conductor segment, according to the invention.

As discussed above, with reference to FIGS. 1 and 5B, conductors may be embedded in the non-conductive material of the lead or may be disposed in one or more lumens extending along the lead. In at least some embodiments, at least some conductor segments are disposed in interior lumens in the inner core 504 that are each configured and arranged to receive single conductor segment. FIG. 6A is a schematic transverse cross-sectional view of one embodiment of an inner core 602 of a lead 604. In FIG. 6A, the inner core 602 includes a central lumen 606 and a plurality of interior lumens 608-615. Each interior lumen 608-615 is configured and arranged for an individual first or second conductor segment to extend along at least a portion of the length of each individual interior lumen 608-615. In FIG. 6A, eight circular-shaped interior lumens 608-615 are shown. Thus, for the inner core 602 shown in FIG. 6A, eight conductor segments can be disposed in the interior lumens 608-615. In some embodiments, the eight conductor segments are each eight different conductors. In other embodiments, the eight conductor segments are two segments each (i.e., a first conductor segment and a second conductor segment) of four different conductors.

In at least some embodiments, the number of conductor segments disposed in interior lumens is double the number of conductor segments disposed in exterior segments. Consequently, when each conductor segment is disposed in an individual conductor lumen, there needs to be twice as many interior lumens as exterior lumens.

Figure 6B:
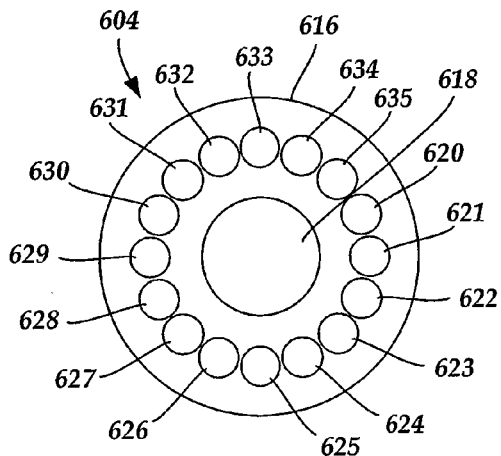
FIG. 6B is a schematic transverse cross-sectional view of another embodiment of an inner core of a lead (or a lead extension), the inner core including a plurality of interior lumens, each interior lumen configured and arranged for housing a single conductor segment, according to the invention.

In at least some embodiments, the number of interior lumens may be doubled from the number of interior lumens of the inner core 602. FIG. 6B is a schematic transverse cross-sectional view of one embodiment of an inner core 616 of the lead 604. In FIG. 6B, the inner core 616 includes a central lumen 618 and a plurality of interior lumens 620-635. Each interior lumen 620-635 is configured and arranged for an individual conductor segment to extend along at least a portion of the length of each individual interior lumen 620-635. In FIG. 6B, sixteen circular-shaped interior lumens 620-635 are shown. Thus, sixteen connector segments can be disposed in the interior lumens 620-633. In some embodiments, one segment of each of sixteen different conductors may be disposed in each of the interior lumens 620-635. In other embodiments, two segments of each of eight different conductors may be disposed in each of the interior lumens 620-635. In at least some embodiments, the diameter of the inner core 616 is no greater than the diameter of the inner core 602.

In at least some embodiments, the diameters of the interior lumens are different from the diameters of the exterior lumens. For example, in at least some embodiments the diameters of the interior lumens are greater than the diameters of the exterior lumens. In at least some embodiments, two conductor segments may be disposed in each of a plurality of interior lumens, while one conductor segment may be disposed in each corresponding exterior segment. Accordingly, in embodiments where there are two conductor segments disposed in each interior lumen and one conductor segment disposed in each exterior lumen, the number of interior lumens may be equal to the number of exterior lumens.

Figure 7A:
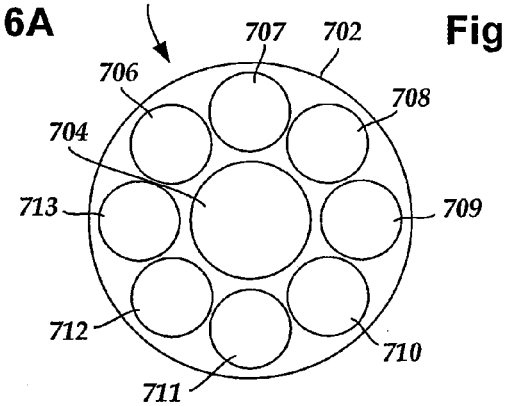
FIG. 7A is a schematic transverse cross-sectional view of one embodiment of an inner core of a lead (or lead extension), the inner core including a plurality of interior lumens, each interior lumen configured and arranged for housing multiple conductor segments, according to the invention.

FIG. 7A is a schematic transverse cross-sectional view of a second embodiment of an inner core 702 of the lead 604. In FIG. 7A, the inner core 702 includes a central lumen 704 and a plurality of interior lumens 706-713. Each interior lumen 706-713 is configured and arranged for multiple conductor segments to extend along at least a portion of the length of each individual interior lumen 706-713. In FIG. 7A, eight circular-shaped interior lumens 706-713 are shown, with each interior lumen 706-713 configured and arranged for two conductor segments to extend along at least a portion of each interior lumen 706-713. In some embodiments, one conductor segment of each of sixteen different conductors may be disposed in each of the interior lumens 706-713. In other embodiments, two conductor segments of each of eight different conductors may be disposed in each of the interior lumens 706-713, while one intermediate conductor segment may be disposed in an exterior segment. In at least some embodiments, two conductor segments of the same conductor may be disposed in each of the interior lumens 706-713. In at least some embodiments, the diameter of the inner core 702 is no greater than the diameter of the inner core 602.

Figure 7B:
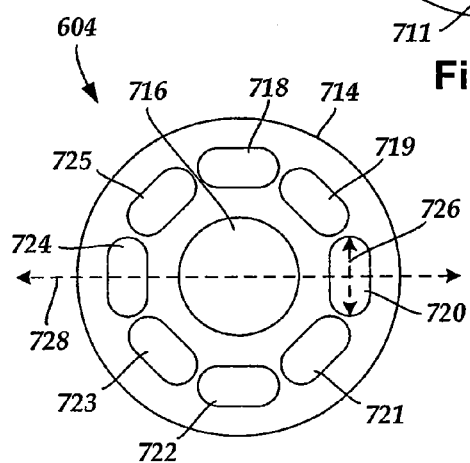
FIG. 7B is a schematic transverse cross-sectional view of a second embodiment of an inner core of a lead (or lead extension), the inner core including a plurality of interior lumens, each interior lumen configured and arranged for housing multiple conductor segments, according to the invention.

In at least some embodiments, the interior lumens may have non-circular transverse cross-sectional shapes. FIG. 7B is a schematic transverse cross-sectional view of an inner core 714 of the lead 604. In FIG. 7B, the inner core 714 includes a central lumen 716 and a plurality of interior lumens 718-725. Each interior lumen 718-725 is configured and arranged for multiple conductor segments to extend along at least a portion of the length of each individual interior lumen 718-725. In FIG. 7B, eight oval-shaped interior lumens 718-725 are shown, with each interior lumen 718-725 configured and arranged for two conductor segments to extend along each interior lumen 718-725. In some embodiments, one conductor segment of each of sixteen different connectors may be disposed in each of the interior lumens 718-725. In other embodiments, two conductor segments of each of eight different conductors may be disposed in each of the interior lumens 718-725, while one intermediate conductor segment may be disposed in an exterior segment. In at least some embodiments, two conductor segments of the same conductor may be disposed in each of the interior lumens 718-725. In at least some embodiments, the diameter of the inner core 714 is no greater than the diameter of the inner core 602.

In FIG. 7B, the interior lumens 718-725 each include a major axis, such as the major axis 726, of the interior lumen 720. In FIG. 7B, the interior lumens 718-725 are oriented such that the major axis of each of the interior lumens 718-725 is approximately perpendicular to a diameter of the inner core 714 which passes through a center of each of the interior lumens 718-725. For example, in FIG. 7B, the major axis 726 of the inner conductive lumen 720 is approximately perpendicular to the diameter 728 extending through the center of the interior lumen 720.

Figure 7C:
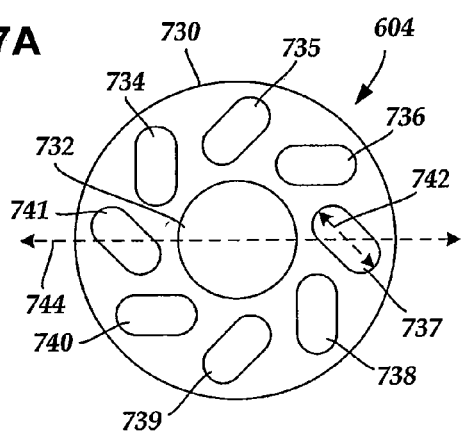
FIG. 7C is a schematic transverse cross-sectional view of a third embodiment of an inner core of a lead (or lead extension), the inner core including a plurality of interior lumens, each interior lumen configured and arranged for housing multiple conductor segments, according to the invention.

In at least some embodiments, the orientation of the non-circular interior lumens may rotated to increase the distance between adjacent interior lumens. FIG. 7C is a schematic transverse cross-sectional view of an inner core 730 of the lead 604. In FIG. 7C, the inner core 730 includes a central lumen 732 and a plurality of interior lumens 734-741. Each interior lumen 734-741 is configured and arranged for multiple conductor segments to extend along the length of each individual interior lumen 734-741. In FIG. 7C, eight oval-shaped interior lumens 734-741 are shown, with each interior lumen 734-741 configured and arranged for two conductor segments to extend along at least a portion of each interior lumen 734-741. In some embodiments, one conductor segment of each of sixteen different connectors may be disposed in each of the interior lumens 734-741. In other embodiments, two conductor segments of each of eight different conductors may be disposed in each of the interior lumens 734-741, while one intermediate conductor segment may be disposed in an exterior segment. In at least some embodiments, two conductor segments of the same conductor may be disposed in each of the interior lumens 734-741. In at least some embodiments, the diameter of the inner core 730 is no greater than the diameter of the inner core 602.

In FIG. 7C the interior lumens 734-741 each include a major axis, such as the major axis 742 of the outer lumen 737. The interior lumens 734-741 may be oriented such that the major axis of each of the interior lumens 734-741 is disposed at a non-perpendicular angle with respect to a diameter of the inner core 730 which passes through a center of each of the interior lumens 734-741. For example, in FIG. 7C the major axis 742 of the outer lumen 737 is disposed at a non-perpendicular angle with respect to the diameter 744 extending through the center of the outer lumen 737. In at least some embodiments, each of the interior lumens 734-741 are disposed at an angle in the range of 15 to 75 degrees or 30 to 60 degrees, for example, at approximately a 45° angle, with respect to a diameter passing through a center of each of the interior lumens 734-741.

It will be understood that the number of conductor segments that can be disposed in an interior lumen may vary. For example, there can be one, two, three, four, five, six, seven, eight, nine, ten, twelve, fourteen, sixteen, or more conductor segments disposed in an interior lumen. As will be recognized, other numbers of conductor segments may also be disposed in an interior lumen.

Figure 8A:
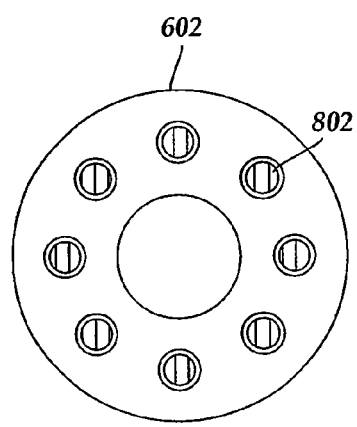
FIG. 8A is a schematic transverse cross-sectional view of one embodiment of the inner core of the lead (or lead extension) shown in FIG. 6A, the inner core including a plurality of interior lumens, each interior lumen housing a single conductor segment, according to the invention.
Figure 8B:
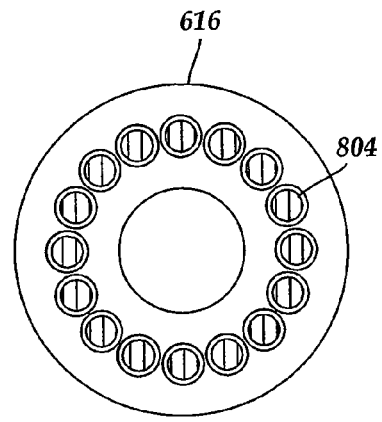
FIG. 8B is a schematic transverse cross-sectional view of one embodiment of the inner core of the lead (or lead extension) shown in FIG. 6B, the inner core including a plurality of interior lumens, each interior lumen housing a single conductor segment, according to the invention.
Figure 9A:
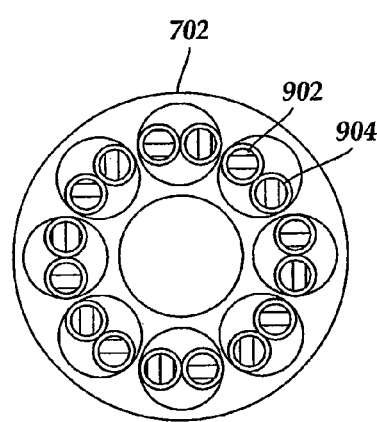
FIG. 9A is a schematic transverse cross-sectional view of one embodiment of the inner core of the lead (or lead extension) shown in FIG. 7A, the inner core including a plurality of interior lumens, each interior lumen housing a plurality of conductor segments, according to the invention.
Figure 9B:
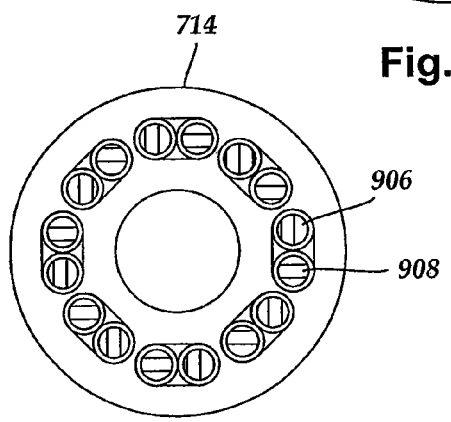
FIG. 9B is a schematic transverse cross-sectional view of one embodiment of the inner core of the lead (or lead extension) shown in FIG. 7B, the inner core including a plurality of interior lumens, each interior lumen housing a plurality of conductor segments, according to the invention.
Figure 9C:
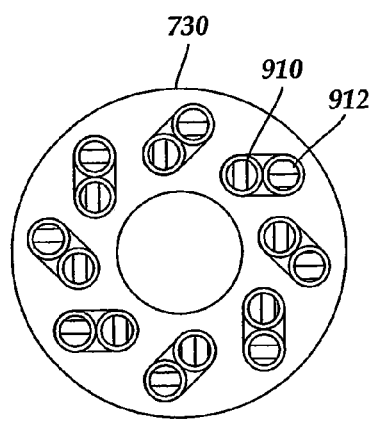
FIG. 9C is a schematic transverse cross-sectional view of one embodiment of the inner core of the lead (or lead extension) shown in FIG. 7C, the inner core including a plurality of interior lumens, each interior lumen housing a plurality of conductor segments, according to the invention.

FIG. 8A is a schematic transverse cross-sectional view of one embodiment of a conductor segment, such as conductor segment 802, disposed in each interior lumen of the inner core 602. FIG. 8B is a schematic transverse cross-sectional view of one embodiment of a conductor segment, such as conductor segment 804, disposed in each interior lumen of the inner core 616. FIG. 9A is a schematic transverse cross-sectional view of one embodiment of multiple conductor segments, such as conductor segments 902 and 904, disposed in each interior lumen of the inner core 702. FIG. 9B is a schematic transverse cross-sectional view of one embodiment of multiple conductor segments, such as conductor segments 906 and 908, disposed in each interior lumen of the inner core 14. FIG. 9C is a schematic transverse cross-sectional view of one embodiment of multiple conductor segments, such as conductor segments 910 and 912, disposed in each interior lumen of the inner core 730. For FIGS. 9A-9C, in some embodiments, one segment of different conductors may be disposed in each interior lumen, while in other embodiments, two segments of the same conductor may be disposed in each of the interior lumens.

Figure 10:
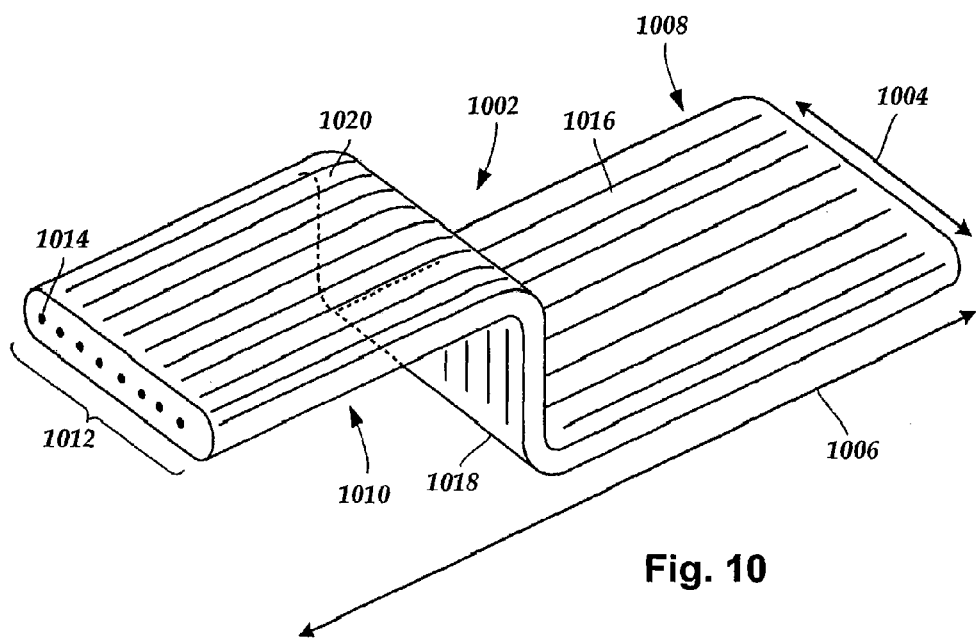
FIG. 10 is a schematic perspective view of one embodiment of a multi-conductor ribbon suitable for use as a coiled conductor guide for wrapping around an inner core of a lead (or a lead extension), according to the invention.

In at least some embodiments, coiled conductor guides and coiled conductor segments disposed in the coiled conductor guides may be implemented by employing one or more multi-conductor ribbons. A multi-conductor ribbon includes a plurality of conductors coupled together by a shared insulation. FIG. 10 is a schematic perspective view of one embodiment of a multi-conductor ribbon 1002 suitable for use as a coiled conductor guide. The multi-conductor ribbon 1002 has a width, represented in FIG. 10 as a two-headed arrow 1004, and a longitudinal length, represented in FIG. 10 as a two-headed arrow 1006. Typically, the longitudinal length 1006 of the multi-conductor ribbon 1002 is much greater than the width 1004 of the multi-conductor ribbon 1002. The multi-conductor ribbon 1002 includes a first end 1008 and a second end 1010 opposite to the first end 1008. A plurality of longitudinally-oriented conductors 1012, such as conductor 1014, are provided along the longitudinal length 1006 and disposed within a shared insulation 1016. In at least some embodiments, the conductors 1012 are configured and arranged as a single layer of conductors 1012. In other embodiments, there can be multiple layers of conductors.

The conductors 1012 can be formed using any conductive, biocompatible material. Examples of suitable materials include metals, alloys, conductive polymers, conductive carbon, and the like, as well as combinations thereof. The insulation 1016 can be formed using any non-conductive, biocompatible material. Examples of suitable materials include silicone, polyurethane, ethylene, tetrafluoroethylene, polytetrafluoroethylene, polydimethylsiloxane, and the like. The multi-conductor ribbons 1002 may be formed in the desired shape by any process including, for example, molding (including injection molding), casting, extrusion, dip coating, and the like.

In FIG. 10, eight conductors 1012 are shown as an exemplary number of conductors 1012 disposed in the multi-conductor ribbon 1002. However, any number of conductors 1012 can be disposed in a multi-conductor ribbon 1002. For example, there can be two, four, six, eight, ten, twelve, fourteen, sixteen, thirty-two, sixty-four, or more conductors 1012. As will be recognized, other numbers of conductors 1012 may be disposed in a multi-conductor ribbon 1002.

In at least some embodiments, the conductors 1012 and the insulation 1016 are flexible and can be bent in multiple directions. For example, in FIG. 10, the multi-conductor ribbon 1002 includes bends 1018 and 1020 in the longitudinal axis. In at least some embodiments, the multi-conductor ribbon 1002 may be bent in other ways as well.

Figure 11:
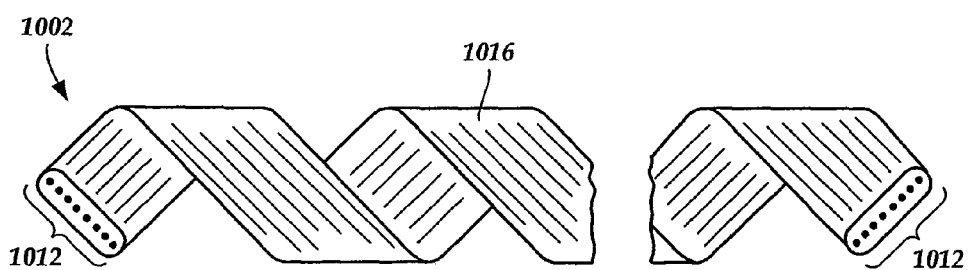
FIG. 11 is a schematic side view of one embodiment of the multi-conductor ribbon shown in FIG. 10 in a coiled position, according to the invention.

FIG. 11 is a schematic side view of one embodiment of the multi-conductor ribbon 1002 in a coiled position. In at least some embodiments, the multi-conductor ribbon 1002 may be wrapped around the inner core (502 in FIG. 5A). In at least some embodiments, the ends of the conductors 1012 can be electrically coupled to the ends of the conductor segments disposed in the interior lumens or to one or more electrodes, conductive contacts, or terminals, as describe above with reference to FIG. 5A. In at least some embodiments, portions of the insulation 1016 surrounding each conductor 1012 may be coupled to the inner core (504 in FIG. 5A).

Figure 12:
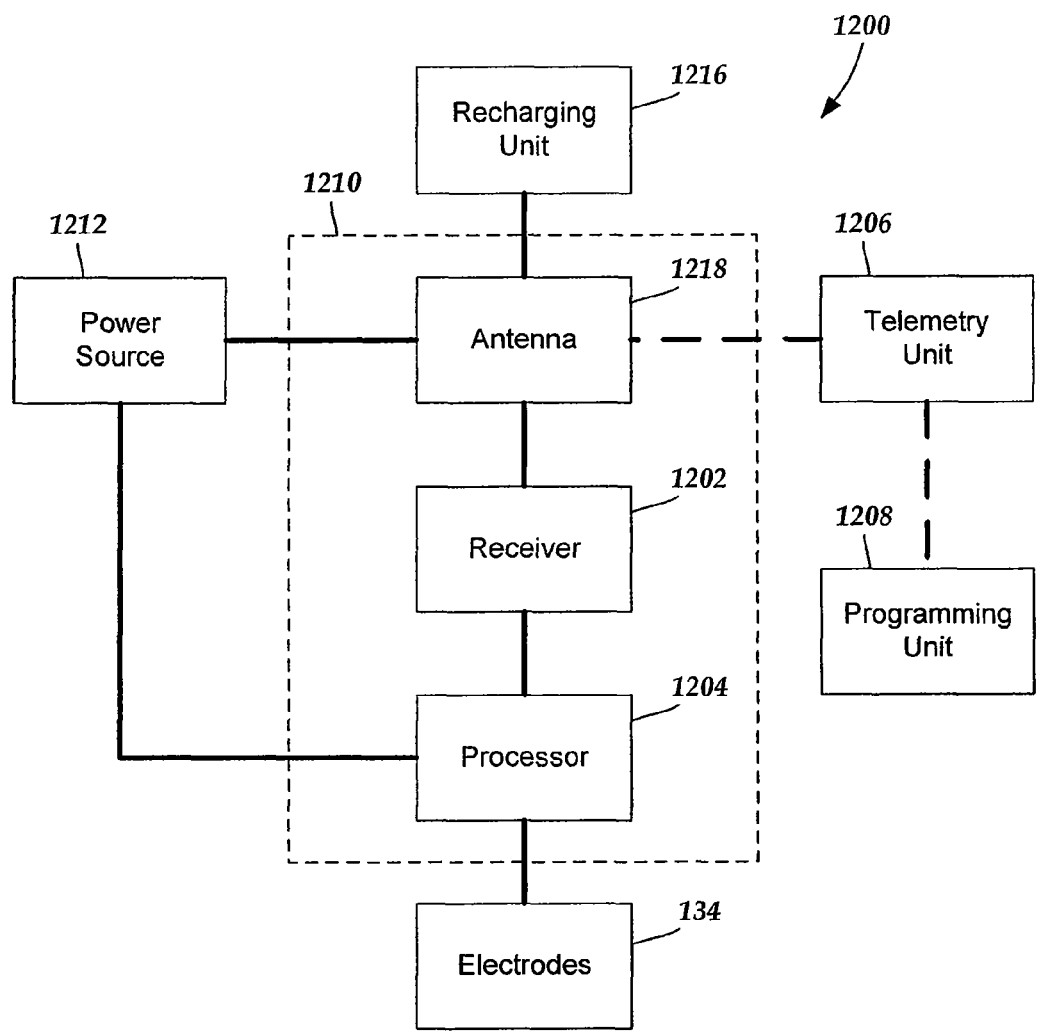
FIG. 12 is a schematic overview of one embodiment of components of a stimulation system, including an electronic subassembly disposed within a control module, according to the invention.

FIG. 12 is a schematic overview of one embodiment of components of an electrical stimulation system 1200 including an electronic subassembly 1210 disposed within a control module. It will be understood that the electrical stimulation system can include more, fewer, or different components and can have a variety of different configurations including those configurations disclosed in the stimulator references cited herein.

Some of the components (for example, power source 1212, antenna 1218, receiver 1202, and processor 1204) of the electrical stimulation system can be positioned on one or more circuit boards or similar carriers within a sealed housing of an implantable pulse generator, if desired. Any power source 1212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1218 or a secondary antenna. The external power source can be in a device that is mounted on the skin of the user or in a unit that is provided near the user on a permanent or periodic basis.

If the power source 1212 is a rechargeable battery, the battery may be recharged using the optional antenna 1218, if desired. Power can be provided to the battery for recharging by inductively coupling the battery through the antenna to a recharging unit 1216 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1204 is generally included to control the timing and electrical characteristics of the electrical stimulation system. For example, the processor 1204 can, if desired, control one or more of the timing, frequency, strength, duration, and waveform of the pulses. In addition, the processor 1204 can select which electrodes can be used to provide stimulation, if desired. In some embodiments, the processor 1204 may select which electrode(s) are cathodes and which electrode(s) are anodes. In some embodiments, the processor 1204 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1208 that, for example, allows modification of pulse characteristics. In the illustrated embodiment, the processor 1204 is coupled to a receiver 1202 which, in turn, is coupled to the optional antenna 1218. This allows the processor 1204 to receive instructions from an external source to, for example, direct the pulse characteristics and the selection of electrodes, if desired.

In one embodiment, the antenna 1218 is capable of receiving signals (e.g., RF signals) from an external telemetry unit 1206 which is programmed by a programming unit 1208. The programming unit 1208 can be external to, or part of, the telemetry unit 1206. The telemetry unit 1206 can be a device that is worn on the skin of the user or can be carried by the user and can have a form similar to a pager, cellular phone, or remote control, if desired. As another alternative, the telemetry unit 1206 may not be worn or carried by the user but may only be available at a home station or at a clinician's office. The programming unit 1208 can be any unit that can provide information to the telemetry unit 1206 for transmission to the electrical stimulation system 1200. The programming unit 1208 can be part of the telemetry unit 1206 or can provide signals or information to the telemetry unit 1206 via a wireless or wired connection. One example of a suitable programming unit is a computer operated by the user or clinician to send signals to the telemetry unit 1206.

The signals sent to the processor 1204 via the antenna 1218 and receiver 1202 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1200 to cease operation, to start operation, to start charging the battery, or to stop charging the battery. In other embodiments, the stimulation system does not include an antenna 1218 or receiver 1202 and the processor 1204 operates as programmed.

Optionally, the electrical stimulation system 1200 may include a transmitter (not shown) coupled to the processor 1204 and the antenna 1218 for transmitting signals back to the telemetry unit 1206 or another unit capable of receiving the signals. For example, the electrical stimulation system 1200 may transmit signals indicating whether the electrical stimulation system 1200 is operating properly or not or indicating when the battery needs to be charged or the level of charge remaining in the battery. The processor 1204 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable lead having a distal end and a proximal end and comprising:
    an inner core with a proximal end, a distal end, and a longitudinal length, the inner core defining a plurality of lumens;
    a plurality of electrodes disposed on the distal end of the lead;
    a plurality of terminals disposed on the proximal end of the lead;
    a plurality of coiled conductor guides, each coiled conductor guide having a first end and a second end, each coiled conductor guide defining a plurality of helical lumens, each coiled conductor guide disposed in a coiled arrangement over a portion of the inner core; and
    a plurality of conductors, each conductor electrically coupling at least one of the electrodes to at least one of the terminals, wherein at least one of the conductors is a first conductor that comprises a plurality emits, each unit comprising
        a first conductor segment of the first conductor extending along the inner core from a beginning point to a first position,
        a coiled conductor segment of the first conductor disposed at least partially in one of the lumens of the coiled conductor guides and extending from the first position to a second position, and
        a second conductor segment of the first conductor extending along the inner core from the second position to an endpoint,
        wherein the first position is between the second position and the endpoint, and the second position is between the beginning point and the first position;
    wherein the diameters of the lumens extending along the inner core are larger than the diameter of the lumens of the coiled conductor guides.

2. An electrical stimulating system comprising:
    the lead of claim 1;
    a control module configured and arranged to electrically couple to the proximal end of the lead, the control module comprising
    a housing, and
    an electronic subassembly disposed in the housing; and
    a connector for receiving the lead, the connector having a proximal end, a distal end, and a longitudinal length, the connector comprising
    a connector housing defining a port at the distal end of the connector, the port configured and arranged for receiving the proximal end of the lead, and
    a plurality of connector contacts disposed in the connector housing, the connector contacts configured and arranged to couple to at least one of the plurality of terminals disposed on the proximal end of the lead.

3. The electrical stimulating system of claim 2, wherein the connector is disposed on the control module.

4. The electrical stimulating system of claim 2, further comprising a lead extension having a proximal end and a distal end, the connector disposed on the distal end of the lead extension.

5. The electrical stimulating system of claim 4, wherein the proximal end of the lead extension is configured and arranged for insertion into another connector.

6. The electrical stimulating system of claim 4, wherein the lead extension has a distal end and a proximal end, the lead extension comprising
    an inner core with a proximal end, a distal end, and a longitudinal length, the inner core defining a plurality of lumens;
    a plurality of conductor contacts disposed on the distal end of the lead extension;
    a plurality of terminals disposed on the proximal end of the lead extension;
    a plurality of coiled conductor guides, each coiled conductor guide having a first end and a second end, each coiled conductor guide defining a plurality of helical lumens, each coiled conductor guide disposed in a coiled arrangement over a portion of the inner core; and
    a plurality of conductors, each conductor electrically coupling at least one of the conductor contacts to at least one of the terminals, wherein at least one of the conductors is a first conductor that comprises a plurality of units, each unit comprising
        a first conductor segment of the first conductor extending along the inner core from a beginning point to a first position,
        a coiled conductor segment of the first conductor disposed at least partially in one of the lumens of the coiled conductor guides and extending from the first position to a second position, and
        a second conductor segment of the first conductor extending along the inner core from the second position to an endpoint,
        wherein the first position is between the second position and the endpoint, and the second position is between the beginning point and the first position.

7. The lead of claim 1, wherein the inner core comprises at least one open section enabling the first conductor to pass between the inner core and at least one of the plurality of lumens of at least one of the plurality of coiled conductor guides.

8. The lead of claim 1, wherein the inner core comprises at least one open section in proximity to each of the first end and the second end of at least one of the coiled conductor guides, the at least one open section configured and arranged to enable the first conductor to pass between the inner core and at least one of the plurality of lumens of the at least one coiled conductor guide.

9. The lead of claim 1, wherein at least one of the coiled conductor guides is coupled to the inner core.

10. The lead of claim 1, wherein at least one of the coiled conductor guides and at least one portion of the at least one conductor disposed within the coiled conductor guide comprise a multi-conductor ribbon.

11. The lead of claim 1, wherein at least one of the lumens extending along the inner core is configured and arranged for housing the first conductor segment and the second conductor segment of at least one of the conductors.

12. The lead of claim 1, wherein at least one of the lumens extending along the inner core is configured and arranged for housing either at least one first conductor segment or at least one second conductor segment.

13. The lead of claim 1, wherein the number of lumens extending along the inner core and housing at least one of the conductor segments is equal to the number of lumens defined in the coiled conductor guides and housing at least one coiled conductor segment.

14. The lead of claim 1, wherein the plurality of units are positioned in series.

15. The lead of claim 1, wherein for each unit, the length of the coiled conductor segment is no more than 1.25 times the combined length of the first conductor segment and the second conductor segment and is at least 0.75 times the combined length of the first conductor segment and the second conductor segment.

16. An implantable lead having a distal end and a proximal end and comprising:
   an inner core with a proximal end, a distal end, and a longitudinal length, the inner core defining a plurality of lumens;
   a plurality of electrodes disposed on the distal end of the lead;
   a plurality of terminals disposed on the proximal end of the lead;
   a plurality of coiled conductor guides, each coiled conductor guide having a first end and a second end, each coiled conductor guide defining a plurality of helical lumens, each coiled conductor guide disposed in a coiled arrangement over a portion of the inner core; and
   a plurality of conductors, each conductor electrically coupling at least one of the electrodes to at least one of the terminals, wherein at least one of the conductors is a first conductor that comprises a plurality of units, each unit comprising
      a first conductor segment of the first conductor extending along the inner core from a beginning point to a first position,
      a coiled conductor segment of the first conductor disposed at least partially in one of the lumens of the coiled conductor guides and extending from the first position to a second position, and
      a second conductor segment of the first conductor extending along the inner core from the second position to an endpoint,
      wherein the first position is between the second position and the endpoint, and the second position is between the beginning point and the first position;
   wherein the number of lumens extending along the inner core and housing at least one of the conductor segments is twice the number of lumens defined in the coiled conductor guides and housing at least one coiled conductor segment.

17. The lead of claim 16, wherein the diameter of at least one of the lumens extending along the inner core is no more than 1.2 times the length of the diameter of at least one of the lumens of the coiled conductor guides and is at least 0.8 times the length of the diameter of at least one of the lumens of the coiled conductor guides.

18. The lead of claim 16, wherein the inner core comprises at least one open section enabling the first conductor to pass between the inner core and at least one of the plurality of lumens of at least one of the plurality of coiled conductor guides.

19. The lead of claim 16, wherein at least one of the coiled conductor guides and at least one portion of the at least one conductor disposed within the coiled conductor guide comprise a multi-conductor ribbon.

20. The lead of claim 16, wherein at least one of the lumens extending along the inner core is configured and arranged for housing the first conductor segment and the second conductor segment of at least one of the conductors.

* * * * *